United States Patent [19]

Cragoe, Jr. et al.

[11] 4,226,867
[45] Oct. 7, 1980

[54] 3,3-SUBSTITUTED SPIRO-1,2,4-BENZOTHIADIAZINES

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 949,348

[22] Filed: Oct. 6, 1978

[51] Int. Cl.$^3$ .................. C07D 285/24; C07D 285/30; A61K 31/54
[52] U.S. Cl. .......................................... 424/246; 544/6
[58] Field of Search ............................. 544/6; 424/246

[56] References Cited

U.S. PATENT DOCUMENTS 3,262,931   7/1966   Cragoe ............................... 260/243

FOREIGN PATENT DOCUMENTS

| | | | |
|---|---|---|---|
| 241464 | 7/1965 | Austria | 544/6 |
| 242144 | 8/1965 | Austria | 544/6 |
| 611464 | 3/1963 | Belgium . | |
| 694380 | 9/1964 | Canada | 544/6 |
| 694388 | 9/1964 | Canada | 544/6 |
| 694389 | 9/1964 | Canada | 544/6 |
| 1162M | 5/1961 | France . | |
| 2387M | 4/1964 | France . | |
| 4027M | 4/1966 | France . | |
| 243875 | 1/1964 | Netherlands . | |
| 927698 | 6/1963 | United Kingdom . | |

*Primary Examiner*—John M. Ford
*Attorney, Agent, or Firm*—Daniel T. Szura; Harry E. Westlake, Jr.

[57] ABSTRACT

3,3-Substituted spiro-1,2,4-benzothiadiazines and their use in treating hypertension are disclosed.

21 Claims, No Drawings

3,3-SUBSTITUTED SPIRO-1,2,4-BENZOTHIADIAZINES

BACKGROUND OF THE INVENTION

The present invention concerns certain 3,3-substituted spiro-1,2,4-benzothiadiazines having antihypertensive activity.

Various 3,3-Spiro-1,2,4-benzothiadiazines represented by the formula

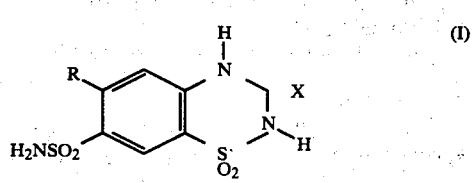

are known Compounds of formula I where X is $C_5$–$C_7$ alkylene are disclosed in British Pat. No. 927,698, Holland Pat. No. 243,875, French Pat. No. 1162M and U.S. Pat. No. 3,097,204. Compounds of formula I where X is an alkyleneheterocycle are disclosed in British Pat. No. 927,698. Compounds where X is

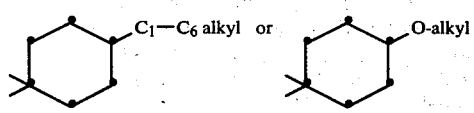

are disclosed in French Pat. No. 2387M and U.S. Pat. No. 3,262,931. The compounds of Formula I are taught to have useful pharmaceutical activity, principally as diuretics, saluretics and the like.

3,3-Substituted spiro-1,2,4-benzothiadiazines wherein the spiro group is

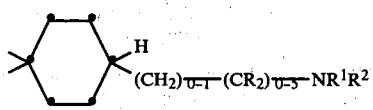

have been discovered. The compounds have useful antihypertensives properties.

SUMMARY OF THE INVENTION 3,3-Amino substituted spiro-1,2,4-benzothiadiazines and use for treating hypertension.

DESCRIPTION OF THE PREFERRED EMBODIMENT

An embodiment of the present invention is compounds of the formula

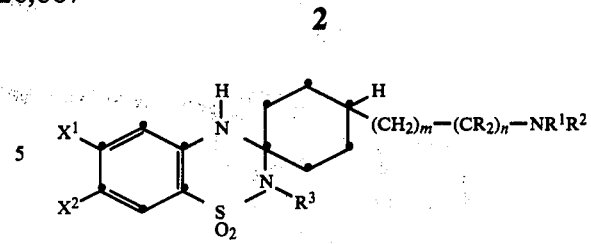

wherein
$X^1$ is H, halo, or trifluoromethyl,
$X^2$ is H, halo or —$SO_2NH_2$,
R is H or lower alkyl,
$R^1$ is H or lower alkyl,
$R^2$ is lower alkyl or cycloalkyl,
$R^1$ and $R^2$ may be joined to form —$(CH_2)$—$_{4\ or\ 5}$,
$R^3$ is H, lower alkyl or aryl,
m is 0 or 1 and,
n is 0 to 5 and non-toxic, pharmaceutically acceptable salts thereof.

As described above, included in the invention are the non-toxic pharmaceutically acceptable salts, preferably the non-toxic pharmaceutically acceptable acid addition salts derived from acids such as hydrochloric acid, hydrobromic acid, hydriodic acid, sulfuric acid, methanesulfonic acid, isethionic acid and the like.

Halo includes Cl or Br, with Cl being preferred.

Lower alkyl includes hydrocarbon $C_1$–$C_6$ alkyl e.g., $CH_3$, —$(CH_2)_5$—$CH_3$, with $C_1$–$C_3$ alkyl being preferred, $CH_3$ being most preferred.

Cycloalkyl includes hydrocarbon $C_3$–$C_6$ alkyl groups e.g., cyclopropyl, cyclohexyl and the like.

Aryl includes phenyl and substituted phenyl, such as chlorophenyl.

$R^1$ and $R^2$ when joined are —$(CH_2)$—$_{4-5}$ which with the N atom form the

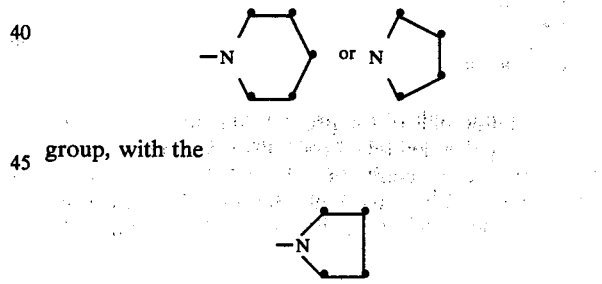

group, with the group being preferred.

The n term indicates 0–5 and m indicates 0–1. Preferred value of m is 0–1 and n is 0–2, with m=0–1 and n=0–1, being more preferred, and m=0 and n=0 being especially preferred.

Preferred compounds have the formula

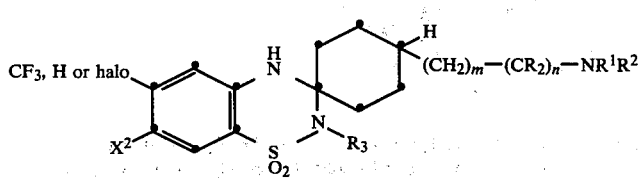

One group of preferred compounds has the formula

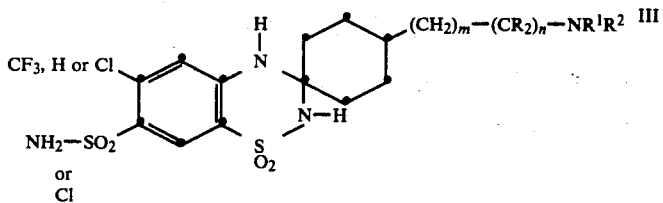

Another group of preferred compounds has the formula

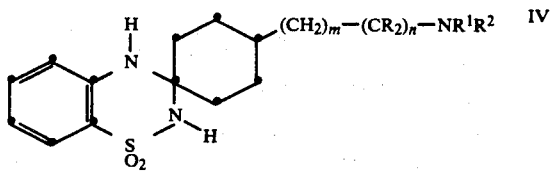

In compounds of Formulae III and IV, the preferred spiro group has m=0-1 and n=0-3, more preferably m=0-1 and n is 0-1, and most preferably m=0 and n=0. Examples of such spiro groups are

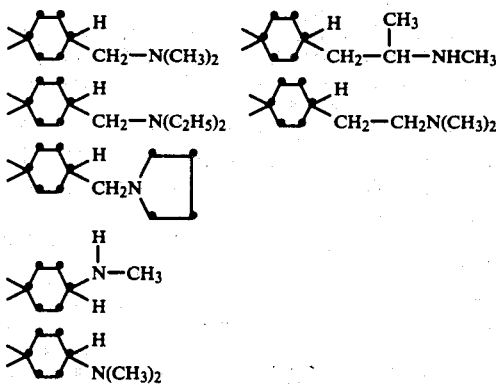

The compounds of the present invention can be prepared using conventional procedures. A general process for preparing the compounds is by condensation of an appropriate aniline with an appropriate ketone (or ketal) as illustrated by the following reaction equation:

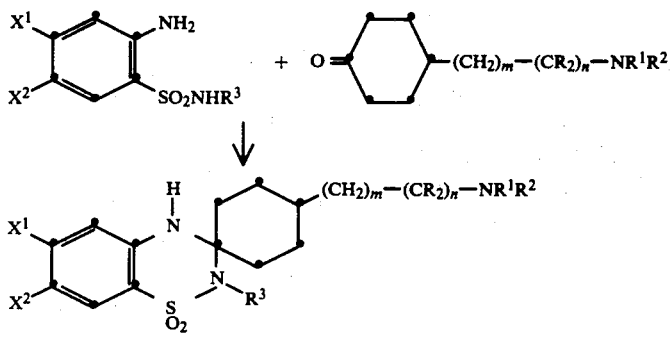

Generally, the reaction is carried out by simply heating a mixture of the aniline with ketone (or ketal) at a temperature sufficient to effect the condensation. Equimolar amounts of the reactants can be used or an excess of the ketone or ketal may be used. Solvents such as ethanol, butanol, or dimethylformamide in the presence of a mineral acid catalyst may be used.

The compounds of the present invention have pharmaceutical activity and are especially useful as antihypertensive agents.

The compounds are effective as antihypertensive agents in hypertensive humans at daily dosages ranging from 1 mg to 5000 mg, preferably from 5 mg to 500 mg and more preferably from 25 to 250 mg.

The compounds are administered using any convenient route, e.g., orally, parenterally, intramuscularly, by insulfation and the like. The dosage forms used may be varied. For oral administration the compounds can be provided as tablets, capsules, solutions, troches, suspensions, emulsions and the like. For parenteral or intramuscular administration, dosage forms such as solutions, suspensions and emulsions are useful.

The compounds are provided in pharmaceutical compositions prepared using conventional compounding procedures—and the dosage forms may include conventional compounding ingredients (i.e. carriers, diluents) such as sterile water, emulsifying agents, starches, sweeteners and the like. The compositions containing the compounds are another embodiment of this invention.

The following examples illustrate preparation of the formula I compounds. All temperatures are in ° Celsius.

EXAMPLE 1

4'-Methylamino-6-chlorospiro[2H-1,2,4-benzothiadiazine-3(4H),1'-cyclohexane]-7-sulfonamide-1,1-dioxide hydrochloride A mixture of 4-amino-6-chloro-1,3-benzenedisulfonamide—(1.0 g., 0.0035 mole) and 4-methylaminocyclohexanone (0.6 g., 0.0047 mole) in 2 N ethanolic hydrochloric acid (5 ml.) is heated at reflux for one hour and cooled to give 1.3 g. of 4'-methylamino-6-chlorospiro[2H-1,2,4-benzothiadiazine-3(4H),1'-cyclohexane]-7-sulfonamide-1,1-dioxide hydrochloride which melts at 288°–90° C.

EXAMPLE 2

4'-Dimethylamino-6-chlorospiro[2H-1,2,4-benzothiadiazine-3(4H),1'-cyclohexane]-7-sulfonamide-1,1-dioxide A mixture of 4-amino-6-chloro-1,3-benzenedisulfonamide (5.72 g., 0.02 mole) and 4-dimethylaminocyclohexanone (3.38 g., 0.022 mole) in 2 N ethanolic HCl (100 ml) is refluxed for one hour and cooled. 4'-Dimethylamino-6-chlorospiro[2H-1,2,4-benzothiadiazine-3(4H),1'-cyclohexane]-7-sulfonamide-1,1-dioxide hydrochloride is filtered, dissolved in warm water (200 ml.) and treated with aqueous ammonia (1.0 ml.) to give 4'-dimethylamino-6-chlorospiro[2H-1,2,4-benzothiadiazine-3(4H),1'-cyclohexane]-7-sulfonamide-1,1-dioxide which melts at 255° C. after recrystallization from dimethylsulfoxide—H₂O.

EXAMPLE 3

4'-Dimethylaminomethyl-6-chlorospiro[2H-1,2,4-benzothiadiazine-3(4H),1'-cyclohexane]-7-sulfonamide-1,1-dioxide A mixture of 4-amino-6-chloro-1,3-benzenedisulfonamide (5.72 g., 0.02 mole) and 4-dimethylaminomethylcyclohexanone (4.0 g., 0.026 mole) in 2 N ethanolic HCl (100 ml.) is refluxed for one and one half hours and cooled to give 4'-dimethylaminomethyl-6-chlorospiro[2H-1,2,4-benzothiadiazine-3(4H)-1'-cyclohexane]-7-sulfonamide-1,1-dioxide hydrochloride (m.p.=280° C.) which is dissolved in warm water (300 ml.) and treated with aqueous ammonia (2 ml.) to give 4'-dimethylaminomethyl-6-chlorospiro[2H-1,2,4-benzothiadiazine-3(4H),-1'-cyclohexane]-7-sulfonamide-1,1-dioxide which melts at 273° C.

EXAMPLE 4

4'-Diethylaminomethyl-6-chlorospiro[2H-1,2,4-benzothiadiazine-3(4H),1'-cyclohexane]-7-sulfonamide-1,1-dioxide hydrochloride A mixture of 4-amino-6-chloro-1,3-benzenedisulfonamide (5.72 g., 0.02 mole) and 4-diethylaminomethylcyclohexanone (5.0 g., 0.027 mole) in 2 N ethanolic HCl (100 ml.) is refluxed for 2 hours, cooled and filtered to give 7.5 g. of 4'-diethylaminomethyl-6-chlorospiro[2H-1,2,4-benzothiadiazine-3(4H),1'-cyclohexane]-7-sulfonamide-1,1-dioxide hydrochloride which melts at 292°-4° C.

EXAMPLE 5

4'-(1-Pyrrolidinylmethyl)-6-chlorospiro[2H-1,2,4-benzothiadiazine-3(4H),1'-cyclohexane]-7-sulfonamide-1,1-dioxide hydrochloride A mixture of 4-amino-6-chloro-1,3-benzenedisulfonamide (5.72 g., 0.02 mole) and 4-(1-pyrrolidinylmethyl) cyclohexanone (5.0 g., 0.027 mole) in 2 N ethanolic HCl (100 ml.) is refluxed one and one half hours and cooled to give 8.2 g of 4'-(1-pyrrolidinylmethyl)-6-chlorospiro[2H-1,2,4-benzothiadiazine-3(4H),1'-cyclohexane]-7-sulfonamide-1,1-dioxide hydrochloride which melts at 268°-70° C.

EXAMPLE 6

4'-(2-Dimethylaminoethyl)-6-chlorospiro[2H-1,2,4-benzothiadiazine-3(4H),1'-cyclohexane]-7-sulfonamide-1,1-dioxide A mixture of 4-amino-6-chloro-1,3-benzenedisulfonamide (4.3 g., 0.015 mole) and 4-(2-dimethylaminoethyl) cyclohexanone (3.0 g., 0.018 mole) in 3 N ethanolic HCl (50 ml.) is refluxed for one and one half hours and cooled to give 4'-(2-dimethylaminoethyl)-6-chlorospiro-[2H-1,2,4-benzothiadiazine-3(4H),1'-cyclohexane]-7-sulfonamide-1,1-dioxide hydrochloride (m.p. 279°-81° C.) which is dissolved in warm water (300 ml.) and treated with aqueous ammonia (1 ml.) to give 4'-(2-dimethylaminoethyl)-6-chlorospiro[2H-1,2,4-benzothiadiazine-3(4H),1'-cyclohexane]-7-sulfonamide-1,1-dioxide which melts at 238°-9° C. after recrystallization from dimethylformamide-water.

EXAMPLE 7

4'-(2-Dimethylaminoethyl)-6-trifluoromethylspiro-[2H-1,2,4-benzothiadiazine-3(4H),1'-cyclohexane]-7-sulfonamide-1,1-dioxide hydrochloride A mixture of 4-amino-6-trifluoromethyl-1,3-benzenedisulfonamide (3.19 g., 0.01 mole) and 4-(2-dimethylaminoethyl)cyclohexanone (2.03 g., 0.012 mole) in 3 N ethanolic HCl (40 ml.) is refluxed for one half hour and cooled to give 5.0 g., of 4'-(2-dimethylaminoethyl)-6-trifluoromethylspiro[2H-1,2,4-benzothiadiazine-3(4H),-1'-cyclohexane]-7-sulfonamide-1,1-dioxide hydrochloride which melts at 282°-4° C.

EXAMPLE 8

4'-(2-Methylaminopropyl)-6-chlorospiro[2H-1,2,4-benzothiadiazine-3(4H),1'-cyclohexane]-7-sulfonamide-1,1-dioxide hydrochloride A mixture of 4-(2-methylaminopropyl) cyclohexanone (4.0 g., 0.024 mole) and 4-amino-6-chloro-1,3-benzenedisulfonamide (4.4 g., 0.0154 mole) in 2 N ethanolic HCl (75 ml.) is refluxed for one hour and cooled to give 7.0 g. of 4'-(2-methylaminopropyl)-6-chlorospiro[2H-1,2,4-benzothiadiazine-3(4H)-1'-cyclohexane]-7-sulfonamide-1,1-dioxide hydrochloride which melts at 296° C.

EXAMPLE 9

4'-(2-Dimethylaminoethyl)-7-chlorospiro[2H-1,2,4-benzothiadiazine-3(4H),1'-cyclohexane]-1,1-dioxide hemisemihydrate A mixture of 2-amino-5-chlorobenzenesulfonamide (8.0 g., 0.039 mole) and 4-(2-dimethylaminoethyl)cyclohexanone (13.5 g., 0.08 mole) in 0.6 N ethanolic HCl (110 ml.) is heated at reflux 18 hours. The solvent is evaporated at reduced pressure and the residue dissolved in water (100 ml.) and neutralized with sodium hydroxide to precipitate 4'-(2-dimethylaminoethyl)-7-chlorospiro-[2H-1,2,4-benzothiadiazine-3(4H),1'-cyclohexane]-1,1-dioxide hemisemihydrate which melts at 234°-5° C. after recrystallization from n-propanol.

EXAMPLE 10

4'-(2-Dimethylaminoethyl)-6-chlorospiro[2H-1,2,4-benzothiadiazine-3(4H),1'-cyclohexane]1,1-dioxide hydrochloride A mixture of 2-amino-4-chlorobenzenesulfonamide (5.0 g., 0.024 mole) and 4-(2-dimethylaminoethyl)cyclohexanone (8.5., 0.05 mole) in 0.6 N ethanolic HCl (67 ml.) is refluxed for one and one half hours and cooled to give 5.3 g. of 4'-(2-dimethylaminoethyl)-6-chlorospiro[2H-1,2,4-benzothiadiazine-3(4H),1'-cyclohexane]-1,1-dioxide hydrochloride which melts at 270° C.

A table of representative compounds of the present invention follows:

COMPOUNDS OF THE FORMULA

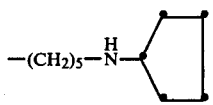

| Example | $X^1$ | $X^2$ | $R^3$ | $-(CH_2)_n-(CR_2)_m-NR^1R^2$ |
|---------|-------|-------|-------|------------------------------|
| 11 | H | H | phenyl | $-(CH_2)_2-NH$-cyclohexyl |
| 12 | Br | H | phenyl | $-CH_2-\overset{CH_3}{\underset{\|}{CH}}-N(C_4H_9)_2$ |
| 13 | Cl | Cl | p-Cl—$C_6H_5$ | $-CH_2-(C_2H_4)-NHCH_3$ |
| 14 | $CF_3$ | Cl | isopropyl | 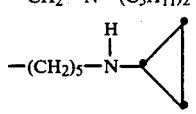 |
| 15 | H | Br | $CH_3$ | $-CH_2-N-(C_5H_{11})_2$ |
| 16 | Br | $SO_2NH_2$ | phenyl | 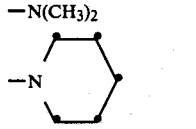 |
| 17 | H | $SO_2NH_2$ | $C_2H_5$ | $-N(CH_3)_2$ |
| 18 | Br | $SO_2NH_2$ | O—Cl—$C_6H_5$ | 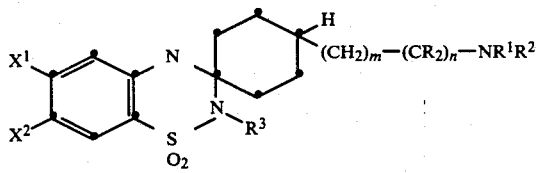 |

Claims to the invention follow.
What is claimed is:
1. A compound of the formula wherein
$X^1$ is H or halo or trifluoromethyl,
$X^2$ is H, halo or $-SO_2NH_2$,
R is H or lower alkyl,
$R^1$ is H or lower alkyl,
$R^2$ is lower alkyl or $C_3$-$C_6$ cycloalkyl
$R^1$ and $R^2$ may be joined to form $-(CH_2)-_4$ or $-(CH_2)_5-$,
$R^3$ is H, lower alkyl, phenyl or chlorophenyl,
m is 0 or 1 and
n is 0 to 5
and pharmaceutically acceptable salts thereof.

2. Compound of claim 1 wherein $X^1$ is H or halo and $X^2$ is halo or $SO_2NH_2$.

3. Compound of claim 2 wherein $X^1$ is H, $X^2$ is Cl and $R^3$ is H.

4. Compound of claim 3 wherein n is 0 to 2.

5. Compound of claim 3 wherein m is 0 and n is 0.

6. Compound of claim 5 wherein $R^1$ is H.

7. Compound of claim 5 where both $R^1$ and $R^2$ are lower alkyl.

8. Compound of claim 7 wherein both $R^1$ and $R^2$ are $CH_3$.

9. Compound of claim 1 wherein R is H.

10. A compound of claim 1 which is 4'-methylamino-6-chlorospiro[2H-1,2,4-benzothiadiazine-3(4H),1'-cyclohexane]-7-sulfonamide-1,1-dioxide and its pharmaceutically acceptable salts.

11. A compound of claim 1 which is 4'-dimethylamino-6-chlorospiro[2H-1,2,4-benzothiadiazine-3(4H),1'-cyclohexane]-7-sulfonamide-1,1-dioxide and its pharmaceutically acceptable salts.

12. A compound of claim 1 which is 4'-dimethylaminomethyl-6-chlorospiro[2H-1,2,4-benzothiadiazine-3(4H),1'-cyclohexane]-7-sulfonamide-1,1-dioxide and its pharmaceutically acceptable salts.

13. A compound of claim 1 which is 4'-diethylaminomethyl-6-chlorospiro[2H-1,2,4-benzothiadiazine-3(4H),1'-cyclohexane]-7-sulfonamide-1,1-dioxide and its pharmaceutically acceptable salts.

14. A compound of claim 1 which is 4'-(1-pyrrolidinylmethyl)-6-chlorospiro[2H-1,2,4-benzothiadiazine-3(4),1'-cyclohexane]-7-sulfonamide-1,1-dioxide and its pharmaceutically acceptable salts.

15. A compound of claim 1 which is 4'-dimethylaminoethyl)-6-chlorospiro[2H-1,2,4-benzothiadiazine-3-(4H)1'-cyclohexane]-7-sulfonamide-1,1-dioxide and its pharmaceutically acceptable salts.

16. A compound of claim 1 which is 4'-(2-dimethylaminoethyl)-6-trifluoromethylspiro[2H-1,2,4-benzothiadiazine-3(4H),1'-cyclohexane]-7-sulfonamide-1,1-dioxide and its pharmaceutically acceptable salts.

17. A compound of claim 1 which is 4'-(2-methylaminopropyl)-6-chlorospiro[2H-1,2,4-benzothiadiazine-3(4H),1'-cyclohexane]-7-sulfonamide-1,1-dioxide and it pharmaceutically acceptable salts.

18. A compound of claim 1 which is 4'(2-dimethylaminoethyl)-7-chlorospiro[2H-1,2,4-benzothidiazine-3(4H),1'-cyclohexane]-1,1-dioxide hemisemihydrate and its pharmaceutically acceptable salts.

19. A compound of claim 1 which is 4'-(2-dimethylaminoethyl)-6-chlorospiro[2H-1,2,4-benzothiadiazine-3-(4H),1'-cyclohexane]1,1-dioxide and its pharmaceutically acceptable salts.

20. A pharmaceutical composition useful for treating hypertension containing a compound of claim 1.

21. A method of treating hypertension by administering an effective amount of a compound of claim 1 to a hypertensive human.

* * * * *